(12) United States Patent
Paturu

(10) Patent No.: US 8,389,483 B2
(45) Date of Patent: Mar. 5, 2013

(54) INTRAUTERINE FETAL GROWTH RESTRICTION—THE TREATMENT MODALITIES FOR CLINICAL RESEARCH, AND THE BIOCHEMICAL RATIONALE

(76) Inventor: Sumathi Paturu, Pleasant Grove, AL (US)

( * ) Notice: Subject to any disclaimer, the term of this patent is extended or adjusted under 35 U.S.C. 154(b) by 505 days.

(21) Appl. No.: 10/460,170

(22) Filed: Jun. 13, 2003

(65) Prior Publication Data

US 2004/0254121 A1    Dec. 16, 2004

(51) Int. Cl.
*A61K 31/7004* (2006.01)
*C07H 3/02* (2006.01)
(52) U.S. Cl. .......................................... 514/23; 536/1.11
(58) Field of Classification Search ...................... 514/23
See application file for complete search history.

(56) References Cited

U.S. PATENT DOCUMENTS 6,576,253 B2 *  6/2003  Manning et al. .............. 424/439

OTHER PUBLICATIONS

Obenshain et al, "Human Fetal Insulin Response to Sustained Maternal Hyperglycemia", The New Englang Journal of Medicine, 283:566-570 (1970).*
Nicolini et al.,"Effects of Fetal Intravenous Glucose Challenge in Normal and Growth Retarded Fetuses", Hormone and Metabolic Research 22(1990) 426-430.*
Beischer et al., "Intrauterine Growth Retardation" Australian and New Zealand Journal of Obstetrics and Gynecology (1983) vol. 23 No. 4 pp. 191-196.*

* cited by examiner

*Primary Examiner* — Eric S Olson

(57) ABSTRACT

Intrauterine Fetal Growth Restriction (IUGR) is a very important clinical problem for which no satisfactory treatment is available so far. The current invention of intravenous (IV) hypertonic glucose supplementation to the mother to improve the glucose transfer to the fetus at the intervillous space by improved facilitated diffusion can be a safe and easy way of treating this problem, as the improved fetal blood glucose can lead to fetal lipogenesis that can conserve the fetal $O_2$ (oxygen) utilization and also relieve the associated metabolic derangements of fetal hypoxia, hypercapnia, and acidosis, apart from replenishing the oxidized coenzymes needed for the carbohydrate metabolism. The use of trans-amniotic fetal feeding studied by animal experiments can be difficult in humans, because of the danger of infection, which can be overcome by the use of implantable ports with a sterile patch technique.

16 Claims, 3 Drawing Sheets

FIGURE - 1, THE MEMRANE TRANSPORT OF GLUCOSE
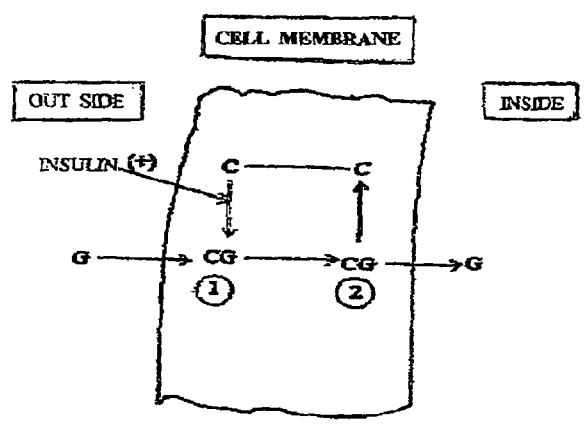

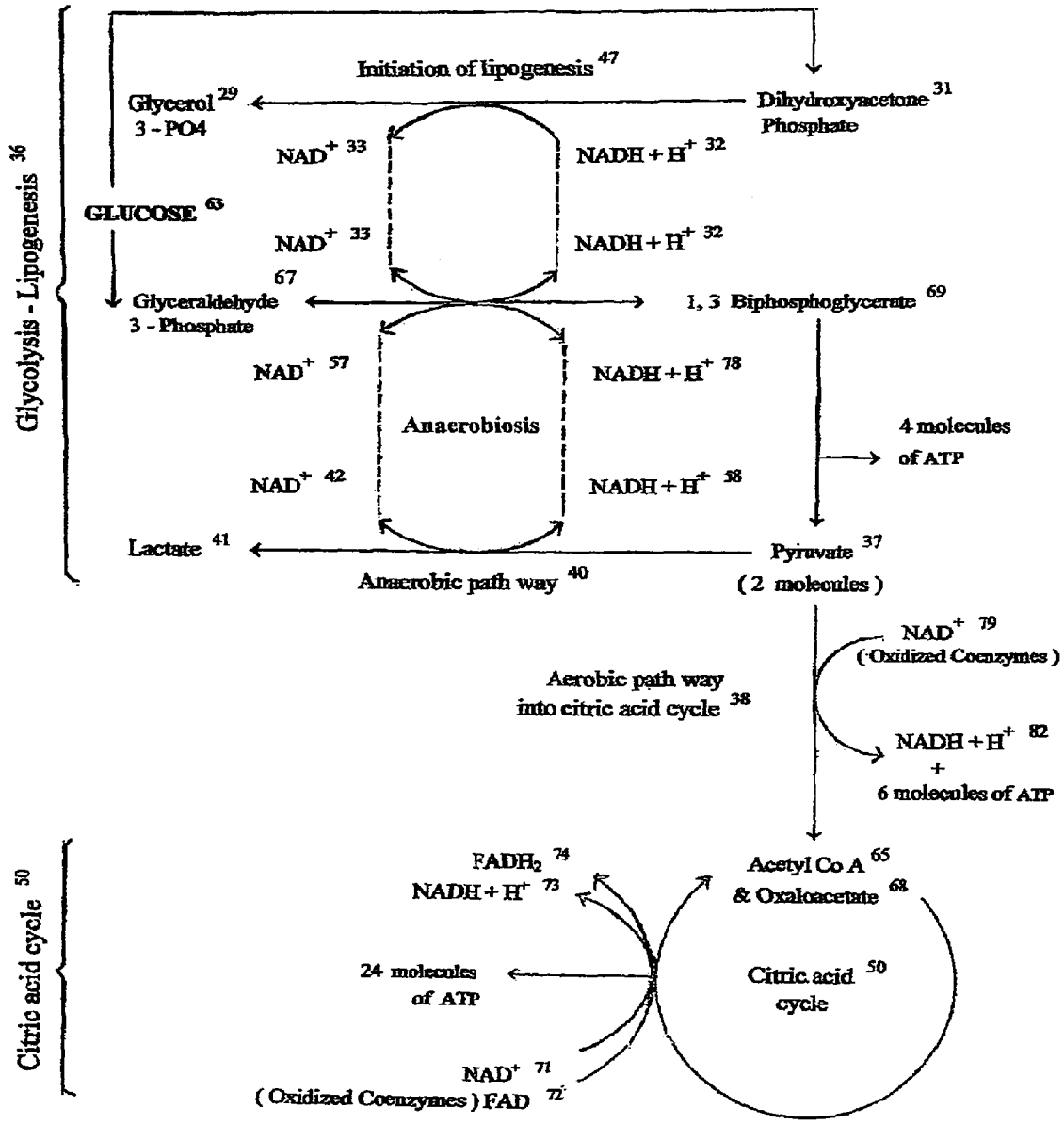

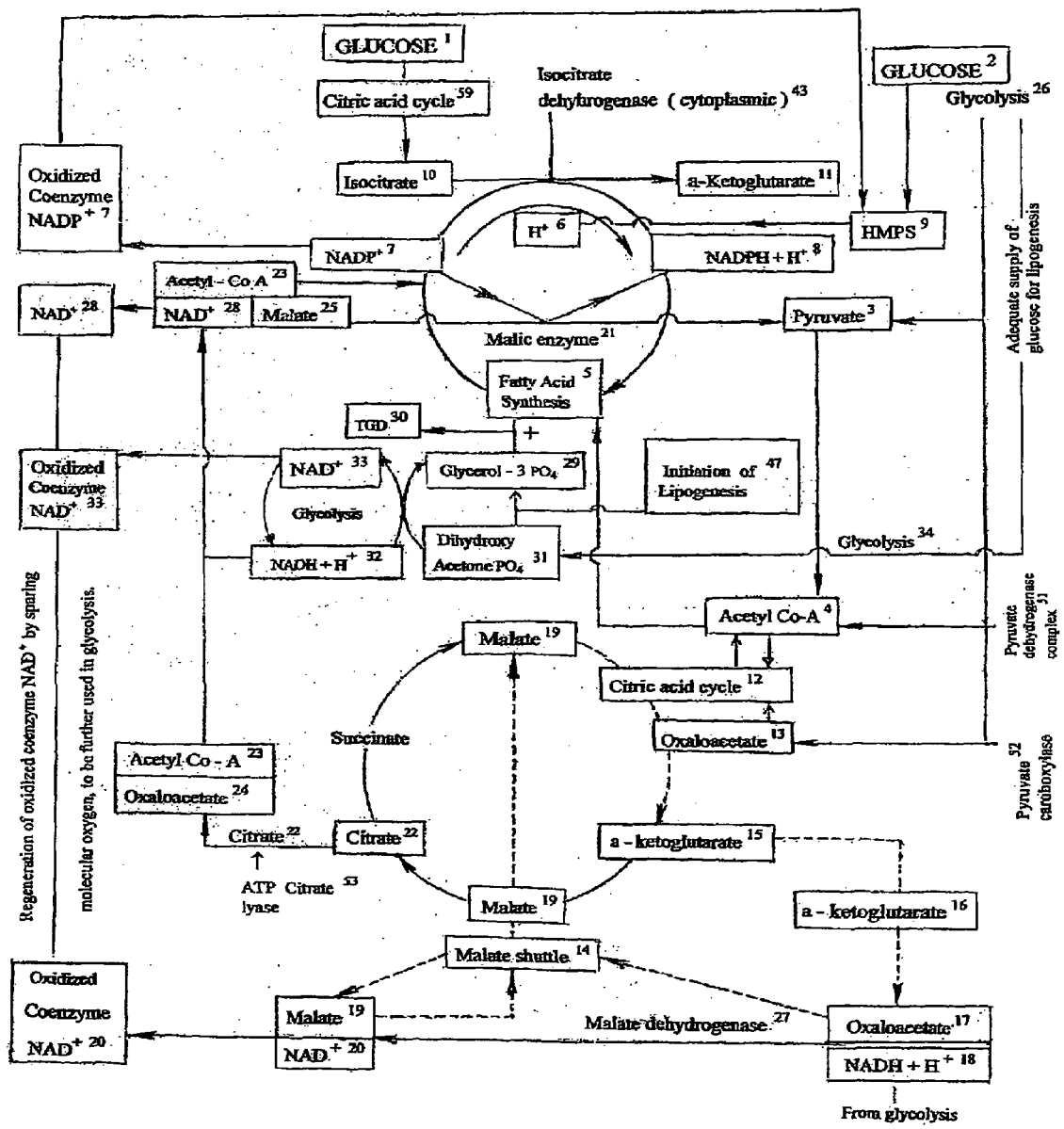

INTRAUTERINE FETAL GROWTH RESTRICTION—THE TREATMENT MODALITIES FOR CLINICAL RESEARCH, AND THE BIOCHEMICAL RATIONALE

INTRODUCTION

This embodiment of invention is directed to novel treatments for 'Intra Uterine Growth Restriction' (IUGR) of a human fetus, one of a long known and incurable (but treatable) maternal-fetoplacental pathology resulting significant mortality and morbidity of the fetus/neonate, it's basic/clinical science research by investigators world wide so far being scant, and clearly disappointing, except for the herein disclosed treatment by the author inventor.

Infants afflicted with intrauterine growth restriction (IUGR) of what ever etiology, or small-for-gestational age (SGA) infants are those whose birth weights are below the tenth percentile for their gestational age.

The maternal diet is the main source of the nutrition supplied to the fetus. There are operational mechanisms in pregnancy to minimize glucose utilization by the mother, there by making it available to the fetus, as glucose is it's prime nutrient. One metabolic action of HPL (Human Placental Lactogen), a hormone normally present in the mother, but not in the fetus, is believed to be blocking the peripheral uptake and utilization of glucose by maternal tissues, while promoting the mobilization and utilization of free fatty acids by the mother. Fats and proteins also are transported across the placenta, but they do not play a major role in fetal nutrition and growth.

The most common cause of intra uterine fetal growth restriction (IUGR) is vascular in nature resulting in the placental insufficiency, thus decreasing the transfer of D-Glucose, (the dextro isomeric form of glucose), the most important fetal nutrient, across the placenta. Accordingly, the disclosure encompasses safe, easy, and a scientifically sound intervention of improving fetal hypoglycemia (a suboptimal blood glucose concentration), and clearly as a result other associated metabolic derangements of placental insufficiency in a surprisingly simple manner.

An accelerated 'Facilitated Diffusion' (described in the following paragraphs) can be achieved by creating a TRANSIENT intermittent hyperglycemia (a term that denotes a rise in blood glucose concentration above specified normal range) in the mother, by intravenous (IV) hypertonic glucose infusion, in an ongoing manner until delivery, as soon as it is confirmed that the IUGR is vascular in orgin.

Chronic vascular disease especially when it is further complicated by superimposed pre-eclampsia commonly causes fetal growth restriction. Chromosomal anomalies are also associated with reduced number of small muscular arteries in the tertiary stem villi. Further, chronic partial placental separation, extensive infarction, circumvillate placenta, velamentous insertion of the cord, one or both the twins affected due to decreased trophoblastic area available to each, to mention a few (as this list by no means is construed to be exhaustive)— are likely responsible for IUGR, and can be similarly improved by maternal IV hypertonic glucose treatment, as earlier specified.

Selective Transfer And Facilitated Diffusion

Although diffusion is an important method of placental transfer, the trophoblast and chorionic villus unit exhibit enormous selectivity in transfer, maintaining different concentrations of a variety of metabolites on the two sides of the villus.

The concentration of a number of substances which are not synthesized by the fetus are several times higher in fetal blood than in the maternal blood. The transfer of D-Glucose across the placenta is accomplished by a carrier mediated, stereospecific, non-concentrating process that can be saturated—said process termed as 'Facilitated diffusion'.

The membrane transport of glucose is illustrated in FIG. 1, and the involved mechanism explained in the following sections.

BRIEF DESCRIPTION OF THE INVENTION

The claimed invention of this disclosure is directed to novel treatments for 'Intra Uterine Growth Restriction' (IUGR) of a human fetus due to placental insufficiency, such treatment involving ongoing intermittent bolus intravenous hypertonic glucose supplementation to the mother, thereby inducing transient intermittent maternal hyperglycemia, which in turn alleviates the chronic fetal hypoglycemia causing growth restriction.

Induced Maternal Hyperglycemia

As previously mentioned, the most common cause of intra uterine fetal growth restriction (IUGR) is vascular in nature resulting in the placental insufficiency, thus decreasing the transfer of D-Glucose, the most important fetal nutrient, across the placenta. There are other adverse metabolic events likely to happen in placental insufficiency, for which the fetus has adaptive devices to counter act the derangements, once hypoglycemia is corrected, where as, there is no such fetal mechanisms to overcome the chronic fetal hypoglycemia of placental insufficiency, that results in fetal growth restriction. The current invention is a physiologically sound way of improving the fetal hypoglycemia, and as a result also other associated metabolic problems of placental insufficiency in a surprisingly simple manner, about which a convincing biochemical discussion is presented in the following pages to justify such proposed treatment.

An earlier discussed, an accelerated facilitated diffusion can be achieved by creating a transient hyperglycemia (induced diabetic state) in the mother by intravenous hypertonic glucose infusion, up to 50-100 cc., in at least 10-20% strength, twice or thrice a day, given as a bolus as soon as it is confirmed that IUGR is of vascular in origin.

The IV infusion as above, creates a situation like a 'fetal meal' during which time deprived fetal circulation can receive more glucose presented in a higher concentration in the same given amount of blood flow across the intervilous spaces. The carrier protein operating in a sub optimal manner before, becomes maximal in its function during the transient maternal hyperglycemic phase. After the fetal energy and growth requirements are met, glucose can be stored in the fetal liver and also in the placenta, to be used by the fetus during the times of need.

Maternal IV hypertonic glucose supplements leading to fetal normoglycemia further resolves multitude of fetal metabolic derangements in the manner outlined below 1. Adequate glucose availability in the fetus enables path way leading to lipogenesis from glycolysis-citric acid cycle, wherein the oxidized co-enzymes $NAD^+$ (Nicotinamide adenine dinucleotide), and $NADP^+$ (Nicotinamide adenine dinucleotide phosphate) regenerated through lipogenesis cause
    (a) glucose to help it's own metabolism to completion, by the regenerated oxidized $NAD^+$, and thereby pyruvate proceeding into citric acid cycle, despite relative fetal hypoxia.

(b) HMPS (hexose monophosphate shunt), a path way source for DNA (deoxy-ribonucleic acid), RNA (ribonucleic acid), and steroids, to continue, by means of sustained supply of oxidized $NADP^+$, regenerated via fatty acid synthesis.

2. By adequate availability, glucose at different steps of it's own metabolism diverts $NADH+H^+$ (reduced form of Nicotinamide adenine dinucleotide plus hydrogen ions) to lipogenesis, from it's otherwise entry into obligatory aerobic oxidative phosphorylation, consistent with the fetus requiring more growth and less ATP (adenosine tri phosphate).

3. Adequate glucose availability induces preferential carbohydrate catabolism in the fetus, thereby obviating beta oxidation of lipids, a high oxygen consuming path way.

4. Adequate glucose availability furthermore relieves fetal hypoxia (deficiency of oxygen reaching the tissues, to a level considered low for optimal body functions) (by means as mentioned above), hypercapnia (the presence of excessive amounts of carbon dioxide in the blood), and acidosis (amount of hydrogen ion concentration in the blood exceeding the normally defined range) including ketoacidosis, and lactic acidosis.

Subsections 1-4 summarized above are elaborately discussed in the section of 'Detailed Description'.

Amniotic Fluid Glucose Supplements

The glucose supplementation to the fetus can also be done by Transamniotic Fetal Nutritional Supplements (TFNS), the studies of which were only done in animal experiments (pregnant rabbits), but can be practically difficult in humans, due to the length of the treatment involved, and the danger of infection likely to be introduced into the amniotic cavity. This difficulty can be overcome by the inventor's novel idea of using implantable ports, that are conventionally used for central venous access, the most recent version of which is the Peripherally Inserted Central Catheter (PICC), that can be implanted at the patient's bed side also, by a simple abdominal subcutaneous pocket or tunnel, the details of which will be enumerated in the Continuation-in-Part (CIP) of this application, soon to be filed.

This technique can be further perfected by making it totally aseptic by using a sterile patch at the site of the port, which can be an alcohol patch supplied in a pouch, before inserting the needle for delivery into, or withdrawal from the amniotic cavity.

BRIEF DESCRIPTION OF DRAWINGS

FIG. 1
Membrane Transport of Glucose.
FIG. 2
Glycolysis and Citric Acid Cycle (Aerobic and Anerobic Pathways, and Coupling with Lipogenesis).
FIG. 3
Adequate glucose availability activating path ways for fatty acid and triglyceride synthesis, generating oxidized coenzymes, and sparing molecular oxygen.
FIG. 1
The Membrane Transport of Glucose 'The Membrane Transport of Glucose' is illustrated in FIG. 1. It shows that glucose (G) combines with carrier protein (C) at point 1, to form a compound CG. CG can penetrate the lipid bi-layer of the cell wall by diffusion, to move to the inner side of the cell membrane at point 2, where glucose G breaks away from the carrier protein C. The carrier protein C returns back to point 1, again to combine with more glucose (G) for continued transport to the inside of the cell (Arthur C. Guyton).

FIG. 2
Glycolysis and Citric Acid Cycle (Aerobic and Anerobic Pathways and Coupling With Lopogenesis)

a) FIG. 2 illustrates the formation of one molecule each of dihydroxy acetone phosphate (31) and glyceraldehyde 3-phosphate (67) from one molecule of glucose (63) during the process of glycolysis-lipogenesis (36).

b) FIG. 2 further shows that dihydroxyacetone phosphate (31) can either initiate lipogenesis (47) by formation of glycerol-3 phosphate (29), OR it can also form glyceroldehyde 3-phosphate (67) (not shown directly in the figure) to be further continued in glycolysis, thus one glucos(63) molecule forming two molecules of glyceraldehydes 3-phosphate (67), and so ultimately two molecules of pyruvate (37) to enter citric acid Cycle (50).

c) FIG. 2 also shows the aerobic (38) and anaerobic (40) pathways of glucose (63) metabolism. Glycolysis can proceed to ultimately produce pyruvate (37), to enter the aerobic (38) pathway. In anaerobic pathway (40), lactate (41) is the end product of pyruvate (37). In aerobic pathway (38), when adequate amount of oxygen is available, acetyl-CoA (65) and oxaloacetate (68) are generated that enter into the citric acid cycle (50) to produce in the entire citric acid cycle (50) 24 molecules of ATP. In anaerobic conditions (40) only a total of 2 molecules of ATP are produced from one molecule of glucose, where as, a total of 38 molecules of ATP are produced in aerobic conditions (38), with glycolysis and citric acid cycle (50) put together.

d) FIG. 2 further shows how adequate glucose availability by generating glycerol-3 $PO_4$ (29) and $NAD^+$ (33) in the cytosol (also the site of lipogenesis), allow glycolysis to proceed even in anaerobic conditions to ultimately generate pyruvate (37) rather than lactate (41), thus 'glucose compensating for lack of oxygen', a concept crucial for the understanding of how mere fetal normoglycemia can target not only the fetal growth but also compensates for the associated hypoxia. During anaerobiasis (40), oxidation of $NADH+H^+$ (78, 58) to $NAD^+$ (42, 57) is coupled with the reduction of pyruvate (37) to lactate (41), which is averted during glucose availability due to the continuous supply of $NAD^+$ (33) from lipogenesis (47), when oxidation of $NADH+H^+$ (32) to $NAD^+$ (33) is coupled to conversion of dihydroxy acetone phosphate (31) to glycerol 3-phosphate (29). Accordingly, in contrast to obligatory anaerobiasis consequent to fetal hypoxia, in the therapeutic setting of normoglycemia lactic acidosis is averted, and the citric acid cycle is made possible.

e) Also shown are that the co-enzymes $NAD^+$ (71), and flavine adenine dinucleotide (FAD)(72) are being reduced to $NADH+H^+$ (73), and reduced form of flavine adenine dinucleotide $(FADH_2)$(74) in the citric acid cycle (50).

FIG. 3
Adequate Glucose Availability Activating Pathways for Fatty Acid and Triglyceride Synthesis Generating Oxidized Coenzymes, and Sparing of Molecular Oxygen FIG. 3 shows that adequate amount of glucose availability represented as box (2), leads to the following pathways 1. Adequate Glucose availability (2) leads for glucose (2) to be converted into acetyl Co-A (4, 23), the precursor for fatty acid synthesis (5).

2. Adequate glucose availability causes coupling of glycolysis (26, 34) citric acid cycle (12) with lipogenesis (47). Accordingly, the Embden Meyerhof pathway of glycolysis (26, 34) taking place in the cytosol is set to produces dihydroxy acetone phosphate (31), an intermediary product which can be converted into glycerol 3-phosphate (29), by glycerol 3- phosphate dehydrogenase, with the help of $NADH+H^+$ (32), which is oxidized to NAD⁺ (33), which in turn can be utilized in glycolysis. Adequate circulating levels of insulin, as in the set up of normoglycemic conditions can activate the triglyceride (TGD)(30) formation in the adipose tissue, by activating the acylation of glycerol-3 phosphate (29).

3. Additionally, Hexose monophosphate shunt (HMPS) (9) is also shown, where in, from the shunt hydrogen (6) is added to NADP⁺ (7) to generate NADPH+H⁺(reduced phosphorylated form of nicotinamide adenine dinucleotide plus hydrogen ion) (8), which is primarily used in fatty acid synthesis (5).

4. FIG. 3 further shows that NAD⁺ (28) is generated from NADH+H⁺ (32) through the function of dehydrogenase enzyme complexes, in the pathways leading to lipogenesis in the extra mitochondrial cytosol, where in, oxaloacetate (24) is converted into malate (25) by malate dehydrogenase complex (27), this step linked to the transfer of reducing equivalents via malic enzyme (21) (NADP malate dehydrogenase present in the cytosol) to NADP⁺ (7), thereby generating NADPH+H⁺ involved in fatty acid synthesis (5), which is also extra mitochondrial. This path way is the means of transferring reducing equivalents from extra mitochondrial NADH+H⁺ (32) to extra mitochondrial NADP⁺ (7) generating NAD⁺ (28) (further used in glucose metabolism), where as, the NADPH+H⁺ (8) and Acetyl-Co A are used in fatty acid synthesis (5). This pathway is important as the link between, and in the perpetuation of carbohydrate and lipid metabolisms thus saving and sparing molecular oxygen, that is crucial to the problem of placental insufficiency, and is a depicted feature of significant importance in FIG. 3.

Activation of fatty acid synthesis (5) and glycerol-3 phosphate synthesis by adequate glucose availability (2, 26) can thus generate oxidized coenzyme NAD⁺ (33) continuously as emphasized in FIG. 3, by which glucose (63) also as shown in FIG. 2 helps it's own metabolism to completion, to produce pyruvate (37) instead of lactate (41), that can proceed into citric acid cycle (50).

Provided in the left part of the FIG. 3 are NADP⁺ (7), and NAD⁺ (33, 28, 20) the oxidized coenzymes, saved in different steps of the intimately interrelated pathways of the carbohydrate and the lipid metabolisms, made possible by perpetuation of lipogenesis (by initiation of lipogenesis (47), fatty acid synthesis 5, glycerol-3 PO₄ synthesis (29), and TGD synthesis (30) by adequate glucose availibility. The NADH+H⁺ oxidized through dehydrogenase enzyme complexes (malate dehydrogenase, and glycerol-3 PO₄ dehydrogenase) at different interactions described obviated it's otherwise entry into the mitochondrial respiratory chain, where the requirement of molecular oxygen is mandatory. Such scheme of operation, as shown in FIG. 3 is consistent with the profound fetal growth in utero, and only insignificant energy requirements, namely ATP.

FIG. 3 also shows the Malate shuttle. Acetyl-CoA (4), formed from glucose (2), further participates in the citric acid cycle (12), along with oxaloacetate (13) (also produced from pyruvate by pyruvate carboxylase). Adequate amounts of oxaloacetate can participate in malate shuttle (14) through the formation of alpha (a) —ketoglutarate (15). It diffuses into the cytosol, and the a—ketoglutarate (16) in the cytosol can form oxaloacetate (17), that will react with NADH+H⁺ (18) from glycolysis, to form malate (19) and NAD⁺ (20). The high lighted (dotted) part of the cycle depicts the malate shuffle through the cytosol and the mitochondrion, and in this shuttle reducing equivalents are transferred from the cytosol to the mitochondrion. The formation of a—ketoglutarate (15, 16) is necessary, as oxaloacetate (13) can not pass through the mitochondrial membrane. Acetyl-CoA, the main building block of fatty acid synthesis, also can not diffuse readily into extra mitochondrial compartment, and so the citrate (22) from the cilric acid cycle (12) diffuses into the cytosol, where it undergoes cleavage by ATP citrate lyase (53) (the citrate cleaving enzyme) to form acetyl-CoA (23) and oxaloacetate (24).

DETAILED DESCRIPTION

This embodiment of invention is directed to novel treatments for 'Intra Uterine Growth Restriction' (IUGR) of a human fetus due to placental insufficiency, such treatments mainly involving ongoing intermittent bolus intravenous hypertonic glucose supplementation to the mother, thereby inducing transient intermittent maternal hyperglycemia, which in turn alleviates the chronic fetal hypoglycemia causing growth restriction.

The most common cause of intra uterine fetal growth restriction is vascular in nature, resulting in placental insufficiency, and thus decreased transfer of D-Glucose, the most important fetal nutrient across the placental interface. There are other metabolic derangements also caused by placental insufficiency for which the fetus has inherent adaptive devices to counter act such problems. How ever, the placenta is the only source of glucose supply to the fetus, and it is severely affected in placental insufficiency. The current invention of treatment is a means of improving the concentration of glucose presented at the placental interface, resulting in an 'accelerated facilitated diffusion' described earlier, thereby improving the chronic fetal hypoglycemia that further resolves the other metabolic derangements of the disease in a surprisingly simple manner, about which a very detailed biochemical discussion is herein presented, with out which the scientific basis of the current invention can not be properly understood.

A discussion of placental physiology is relevant to the understanding of the proposed treatment as a subject of this disclosure.

Placental Physiology

Although diffusion is an important method of placental transfer, the trophoblast and chorionic villus unit exhibit enormous selectivity in transfer, maintaining different concentrations of a variety of metabolites on the two sides of the villus.

The concentration of a number of substances which are not synthesized by the fetus are several times higher in fetal blood than in the maternal blood. The transfer of D-Glucose across the placenta is accomplished by a carrier mediated, stereospecific, non-concentrating process that can be saturated—'Facilitated diffusion'. Transfer proteins for D-Glucose, GLUT—1 and GLUT—3 have been identified in the plasma membrane (the microvilli) of human syncytiotrophoblast. More over, in response to Insulin action, intracellular GLUT—3 is redistributed to the cell plasma membrane.

The membrane transport of glucose across the cell membrane, including placenta is illustrated in FIG. 1. It shows that glucose (G) combines with a carrier protein (C) at point 1 to form the compound CG. This combination is soluble in the lipid so that it can diffuse (or simply move by rotation of the larger carrier molecule) to the other side of the membrane, where glucose breaks away from the carrier protein (point 2), and passes to the inside of the cell while the carrier moves back to the outside surface of the membrane to pick up still some more glucose to transport it also to the inside. Thus the effect of the carrier protein is to make glucose soluble in the membrane; without it glucose can not pass through the membrane.

The rate at which a substance passes through the placental interface by facilitated diffusion is greatly improved by higher (though transient) concentration of the substance on the maternal side of the placenta, and in case of glucose transport, the overall rate being greatly increased also by insulin. Large quantities of insulin (which can be released by pancreas during a meal, or hyperglycemic state) is likely to increase the rate of glucose transport about seven to ten fold, though it is not known if it is caused by an effect of insulin to increase the quantity of the carrier protein in the membrane, or else it increases the rate at which the chemical reaction takes place between glucose and the carrier.

An accelerated facilitated diffusion specified earlier, can be achieved by creating a transient episodic hyperglycemia in the mother by intravenous hypertonic glucose infusion, up to 50-100cc., in at least 10-20% strength, twice or thrice a day, given as a bolus, to induce normoglycemia in the afflicted fetus, as soon as it is confirmed that IUGR is of vascular/placental in origin. Diverse pathological conditions likely fall under this state, and they are similar to what were enlisted under the section of 'Introduction', which how ever, were not construed to be exhaustive.

It is also relevant here to describe more of the feto-maternal metabolism of pregnancy with out which the biochemical and clinical rationale of the current invention can not he adequately explained to the satisfaction of a skeptical reader.

THE FETO-MATERNAL METABOLISM OF PREGNANCY

The Maternal Metabolism

Profound changes occur in maternal carbohydrate and fat metabolism during pregnancy as evidenced by the increased blood levels of lactate, pyruvate, and plasma lipid fractions. Fasting blood sugar is not how ever raised in pregnancy.

It has been generally assumed that carbohydrate tolerance is impaired in pregnancy, and thus pregnancy itself constitutes a diabetogenic stress for the woman. The fact that diabetes may first manifest during pregnancy (it is likely that it could be present earlier, but diagnosed during pregnancy when blood glucose is usually checked for the first time, making the statistical figures of incidence of diabetes during pregnancy more than it's actual prevalence), that the diabetic women frequently require increased amounts of insulin as pregnancy advances, and the occurrence of glycosuria during pregnancy—are all cited as likely evidence in support of this view.

However, the fasting blood sugar is not increased in normal pregnancy, as evidenced by serial studies of carbohydrate tolerance in healthy women during gestation. Tolerance to IV glucose may in fact be improved in early pregnancy compared to what is likely recorded in non pregnant state.

Pregnancy is characterized by major physiological adjustments affecting every system of the body. The changes are frequently in a scale other wise unknown in healthy adult life, and had led wide spread misunderstanding and diagnostic confusion. Unless it is realized that the pregnant woman is physiologically in a different realm, whose health can be gauzed only against the standards of healthy women in the same physiological state, disease will be diagnosed where none exists.

While it is true that the reasons for a decreased 'glucose tolerance', or the more relaxed homeostatic control, possibly can not be explained to the satisfaction of the most skeptical readers, there is no reason for believing it is any thing other than physiological. It can be stated that the maternal changes are purposeful, and directed towards the welfare of the fetus.

Though the carbohydrate tolerance in general is not reduced in normal pregnancy, the peripheral resistance to insulin is increased. Blood insulin levels are in fact raised in pregnancy both in fasting state and after glucose load. This paradox of increased amount of circulating insulin in the organism is due to the presence of additional anti insulin factors—like corticosteroids, catacholamines, and glucagon, but the most important insulin antagonist is the Human Placental Lactogen (HPL), a polypeptide produced by placenta. It cross reacts immunologically with human growth hormone.

HPL, which is produced in enormous quantities in placenta, causes increase in free fatty acids (FFA), and in this respect seems more dominant than insulin, because insulin is anti lipolytic. And once there is increased free fatty acids, the maternal tissues utilize more of them, sparing glucose to be diverted to fetoplacental circulation to be utilized, which is likely a slow process, because the amount of glucose spared from all the tissues of the maternal body is much more and generalized, compared to what is getting into the fetus through only the narrow channel of the umbilical cord (thus the maternal body acts as the glucose reservoir for the sustained glucose supply to the fetus). How ever, as long as there are high levels of glucose, it is going to release insulin from maternal pancreas. The HPL also prevents insulin's effects on the carrier transporters of glucose, apart from increasing free fatty acids that compete with glucose for their own utilization by the maternal tissues.

The maternal pancreas is only conditioned to produce insulin as glycemic response, but does not likely perceive that insulin and also glucose are not being effectively used by the maternal tissues, except the placenta. How ever, this fundamental loop of the body's feed back mechanism which prevails during pregnancy is still not ineffective, because the rise of insulin proportional to the glucose level is needed to enable facilitated diffusion at the utero-placental interface, which the insulin increases by many fold.

Tolerance to intravenous hypertonic glucose supplement is in fact improved during pregnancy—a basis for the proposed treatment It is of common belief that pregnancy is potentially diabetogenic and that tissue resistance to insulin increases, but if the physiology of the cause and effect of the above changes during pregnancy are analyzed, we can say that it is maternal adaptation, rather than tissue resistance, all these adaptive devices being geared to direct glucose to fetus at the expense of the mother, the maternal tissues having changed their way to using FFA more than glucose for energy and growth. These maternal adjustments are the result of a over stretched adaptation even during normal pregnancy—being so many operational devices put together to divert glucose to the fetus, which can not be helped any further during uteroplacental insufficiency, to increase the amount of glucose to be presented at the placental intervillous space, though the fetal circulation is chronically deprived of it's prime nutrients. IV glucose supplementation is some what similar to but easier than what the maternal body tissues in pregnancy are trying very hard to achieve—sparing the mother using glucose, and diverting it to the fetus. IV glucose should only ease the over stretched adaptive pathways of pregnancy. Accordingly, there likely is sufficient theoretical basis to believe that IV glucose supplement is better tolerated in pregnancy than in non pregnant condition. After few days of hospitalization to optimize the glucose supplements needed for any mother, and teaching such involved protocol to the patient, it can be done at home also, with the help of the home health nurse. During the hospitalization it can also be decided if the insulin supplementation is necessary or not. Choosing to give the infusion to the mother in between the meals to make it more tolerable, or physiologically more suitable, is a scientifically very appealing thought. Mid night is also a preferable time, though likely perceived as inconvenient to the mother.

The transitional hyperglycemia in the maternal blood can also help the fetus to build the glycogen stores in the liver, and fat in the subcutaneous adipose tissue, after meeting it's energy requirements. This storage helps the fetus to cope with the possible hypoglycemic episodes. Insulin increases the glycogen deposition in the placenta also, which Claude Bernard compared to early fetal liver, or more appropriately to it's skeletal muscle, because of it's metabolic response to Adrenaline and other hormones—is release of lactate, rather than glucose. How ever, lactate is still utilized by the fetus, especially by the fetal brain.

Fetal Blood Glucose Homeostasis

The fetus and the new born are more resistant to anoxia/hypoxia than the adult. Altered rates of glycolysis, in anaerobic conditions is generally greater than in adult tissues. But the brain that is very sensitive to inference with it's glucose supply, has little glycogen, and has similar rates of glycolysis in aerobic and anerobic conditions. Studies showed that metabolic protection for brain during intra uterine anoxia/hypoxia may be provided by the ability of the fetal and neonatal cerebral tissue to metabolize substrates other than glucose such as pyruvate, lactate, and acetate. The citric acid cycle can proceed in the relative absence of molecular oxygen, provided that adequate supply of oxidized coenzymes are available. In fetal tissues, optimal glucose as in normoglycemia induces synthesis of fatty acids, a process which requires the hydrogen contained in the reduced coenzymes. Oxidized coenzymes would be thus reformed, and enable the pyruvate produced by glycolysis to be metabolized via citric acid cycle, with release of energy (ATP) i.e. coupling of lipogenesis with glycolysis-acid cycle, by which hypoxia is better tolerated.

The resistance of the fetus and neonate to hypoxia probably depends on a number of alterations in metabolic patterns in different tissues, each of which provides a small increase in metabolic efficiency, and hence over all ensures a greater safety margin during oxygen lack. As the human fetus grows, the proportion of Linoleic acid (an essential free fatty acid, not synthesized in the fetal body and comes from the maternal blood) in it's subcutaneous fat decreases, and the proportion of Palmitic acid (produced with in the fetal body) increases, and at the time of birth, Palmitic acid is twice as much as Linoleic acid (N.B. Myant). The fatty acid composition of the subcutaneous fat of the newborn is similar to that of animals given a diet rich in carbohydrate, and poor in fat. Raiha (1954) pointed out that synthesis of fats from carbohydrate may provide the human fetus with means of decreasing it's oxygen requirements. Villee (1954), had estimated that the triglycerides synthesized during last months of fetal life might save the fetus a maximum of ⅛th of the total oxygen requirements. Mylination of the brain is most rapid in the $7^{th}$ month of the fetal life, during which time the human brain would be most susceptible to the effects of under nutrition. Unfortunately, IUGR also is more pronounced at this period of intra uterine life. Cholesterol and other complex lipids are of special importance in the formation of myelin in the developing brain. Fetal tissue can synthesize most (90%) if not all cholesterol from glucose or acetate. In a normal fetus, oxidation of fatty acids (use of fats for energy—i.e. fat catabolism) contributes little towards it's total energy consumption, thus saving substantial amounts of oxygen. It is consistent with the finding that the FFA (free fatty acids) levels are low in normal fetus. The respiratory quotient (RQ)(the ratio of $CO_2$ and $O_2$) of fetal tissues in vitro has also been shown to be above unity (above 1)(Roux 1966), indicating that synthesis of FFA from carbohydrate outweighs oxidation of FFA.

Adequate supply of glucose makes hypoxia more tolerable—the biochemical rationale Ability of the fetus to with stand oxygen lack is related to a particular metabolic change i.e. altered rates of glycolysis and lipogenesis, and indeed the rate of glycolysis in fetal tissues in hypoxic conditions is generally greater than in adult tissue.

1. With limited amounts of oxygen, and also limited amounts of glucose available to the fetus in utero, as in untreated IUGR Glucose metabolism (glycolysis) can proceed up to the production of pyruvate both in anaerobic and aerobic path ways, producing 2 molecules of pyruvate (see the path way in FIG. 2). After this step, the further pathway changes. In anaerobic conditions lactate is the end product of pyruvate with also the formation of coenzyme $NAD^+$. Glucose availability (and induced lipogenesis), by generating glycerol-3 $PO_4$ and also the $NAD^+$ in the cytosoL (also the site of lipogenesis) allow glycolysis to proceed even in relatively hypoxic conditions to ultimately generate pyruvate (37) rather than lactate (41), thus 'glucose compensating for lack of oxygen', a concept crucial to the understanding of how mere fetal normoglycemia can target not only the fetal growth, but also compensates for associated hypoxia. Accordingly, in contrast to obligatory anaerobiasis consequent to fetal hypoxia, in the therapeutic setting of normoglycemia, the lactic acidosis is averted, and the citric acid cycle is made possible. The foregoing fetal devices manipulating carbohydrate-lipid pathways prevailing in normoglycemic conditions to alleviate a relative hypoxia in utero, are obviously not amenable to the fetus in situations of combined hypoxia and hypoglycemia.

With what ever amount of oxygen available, once acetyl Co-A is generated, in the extramitochondrial compartment, fatty acid synthesis can be activated, but further maintenance is only possible by availability of glucose that can initiate hexose mono phosphate shunt (HMP shunt), that is the chief source of the hydrogen required as $NADPH+H^+$, in the reductive synthesis of fatty acids. Other sources of NADPH include the isocitrate dehydrogenase reaction, and the reaction that converts malate to pyruvate catalysed by mailic enzyme (NADP malate dehydrogenase). All these three pathways are also extramitochondrial like the FFA synthesis itself, and involve abundant supply of glucose, that can generate NADPH necessary for fatty acid synthesis, and these are also linked to the generation of $NAD^+$, the oxidized coenzyme necessary for glucose metabolism, making the 'coupling of lipogenesis and glycolysis-citric acid cycle' surprisingly efficient, even with out participation of molecular oxygen in these path ways. How ever, with limited glucose availability in placental insufficiency, the sequence of events stop at the level of the production of pyruvate, and initiation of fatty acid synthesis, both of which can not proceed any further.

2. With limited supply of oxygen, but adequate amounts of glucose available to the fetus in utero, as in treated IUGR In the pathway shown in the FIG. 3, devised by the author, it is shown how a surplus of glucose availability (2) activates both the fatty acid synthesis (5) and TGD (triglyceride) synthesis (30) (and also provide sufficient amount of oxaloacetate 13) —both path ways spare molecular oxygen, and further generate oxidized coenzymes $NAD^+$ and $NADP^+$ that help the maintenance of oxidative pathways like citric acid cycle, glycolysis, and HMPS. Oxygen thus spared in some of these pathways in the fetal body, can be utilized for oxidative phosphorylation, where oxygen requirement is mandatory, to generate the needed ATP for energy.

In FIG. 3, glucose in box (1) shows the initiation of citric acid cycle, and limited amount of fatty acid synthesis, as in no abundant supply of acetyl-CoA or oxaloacetate. Glucose in box (2), denoting the additional amount of glucose available, shows the pathways that are activated and perpetuated by the production of Pyruvate (3), acetyl-CoA (4), oxaloacetate (13), and the NADPH+H$^+$ (8) (through HMPS).

Acetyl-CoA, formed by the pyruvate dehydrogenase complex (51) participates in fatty acid synthesis (5). The hydrogen (6) needed for the co enzyme NADP$^+$ (7) to be converted into NADPH+H$^+$ (8), necessary for the fatty acid synthesis is mostly supplied by the hexose monophoshate shunt (9)(HMPS), that takes place in the extramitochondrial cytosol, also the place for fatty acid synthesis. The HMPS is active in adipose tissue in the presence of high circulating glucose. During fatty acid synthesis NADPH+H$^+$ (8) is oxidized to NADP$^+$ (7). The FIG. 3 also high lights how the most important reaction in lipogenesis i.e. the formation of acetyl-CoA (4), and the NADPH+H$^+$ (8) are initiated by the adequate supply of glucose (2). The NADP$^+$ (7) that is generated in the fatty acid synthesis, can in turn be further used in the HMPS.

The FIG. 3 also shows how the NAD$^+$, the oxidized coenzyme necessary for the metabolism of glucose is also generated during the process of lipogenesis. Acetyl-CoA (4), formed from adequate glucose (2), further participates in the citric acid cycle (12), along with oxaloacetate (13) (also produced from pyruvate by pyruvate carboxylase (52), the enzyme that replenishes oxaloacetate to the citric acid cycle in the presence of biotin). Adequate amounts of oxaloacetate thus formed can participate in malate shuttle (14), through the formation of a-ketoglutarate (15). It diffuses into the cytosol, and the a-ketoglutarate (16) in the cytosol can form oxaloacetate (17) that will react with NADH+H$^+$ (18) (from glycolysis), to form malate (19) and NAD$^+$ (20). The high lighted (dotted) part in FIG. 3 shows the malate shuttle through the cytosol and the mitochondrion, and in this shuttle NAD$^+$ (20) needed for glycolysis is regenerated from NADH+H$^+$. This reaction can also be linked to the reduction of NADP$^+$ (7) NADPH+H$^+$ (8) with the conversion of malate (19, 25) to pyruvate (3) by malic enzyme (21)(not directly shown in the FIG. 3). The formation of a-ketoglutarate (15, 16) is necessary because oxaloacetate (13) can not pass through the mitochondrial membrane.

Acetyl-CoA, the main building block for the fatty acid synthesis, can not diffuse readily into the extramitochondrial compartment, and so the citrate (22) from the citric acid cycle diffuses into the cytosol, where it undergoes cleavage by ATP citrate lyase (the citrate cleaving enzyme) (53), to form acetyl-CoA (23) and oxaloacetate (24). The activity of the citrate cleaving enzyme increases when there is high glucose availability, which also parallels the activity of fatty acid synthesis. Acetyl-CoA (23) formed is there by available for the initiation of fatty acid synthesis, and the oxaloacetat (24) can form malate (25) via NADH+H$^-$ (32) linked malate dehydrogenase (27) forming NAD$^-$ (28), followed by the generation of NADPH+H$^+$ (8), via the malic enzyme (21) with the formation of pyruvate (3). This path way is means of transfering reducing equivalents from extramitochondrial NADH to NADP$^+$ as shown in the FIG. 3. Alternatively, malate can be transported into the mitochondrian where it is able to reform oxaloacetate (13). It is to be noted that the citrate transporter in the mitochondrial membrane requires malate to be exchanged with citrate.

Glycerol—3 phosphate (29), the main ingredient that combines with the FFA (5) to form TGD (30) in the adipose tissue, is derived from the intermediate product of glycolysis—the dihydroxyacetone phosphate (31), which forms the glycerol—3 phosphate (29), by reduction with NADH+H$^+$ (32), catalysed by glycerol—3 phosphate dehydrogenase, also forming NAD$^+$ (33) in the process. The glycerol—3 phosphate (29) combining with the FFA (5) to form the TGD (30) is activated by insulin in glycemic conditions. The NAD$^+$ (33) generated in the lipogenesis can be further utilized in glycolysis and NADH+H$^+$ (32), generated in the glycolysis can in turn be used for further synthesis of glycerol—3 phosphate for lipogenesis.

Both the NAD$^+$ and NADP$^+$ thus formed in the process of lipogenesis, can keep up with the maintenance of glycolysis, and HMPS, the oxidative metabolic pathways of the carbohydrate metabolism, made possible with more utilization of glucose, and less of oxygen. Molecular oxygen thus saved, can be used to generate ATP (the requirement of which is how ever less in the fetus) in oxidative phosphorilation of the respiratory cycle, where in, the participation of the molecular oxygen is mandatory.

In the left part of the figure are the NADP$^+$ and NAD$^+$, the oxidized coenzymes saved in the different steps of the intimately interrelated pathways of the carbohydrate and the lipid metabolism.

The other metabolic derangements in placental insufficiency

It is a legitimate concern that treatment of impaired glucose transfer by inducing transient intermittent hyperglycemic state in the mother can not correct the other problems inherent to the placental insufficiency, and all these problems put together would still be detrimental to the fetal well being. It is also of critical issue that adequate glucose availability in hypoxic conditions can lead to anaerobiosis and lactic acidosis, but these concerns need in depth biochemical exploration. The notorious metabolic problems of placental insufficiency other than hypoglycemia are 1. Hypoxia 2. Hypercapnia 3. Acidosis (including ketoacidosis), and 4. Lactic acidosis, that needs a special and separate mention.

In placental insufficiency the fetus has no means to improve the hypoglycemia, as there are not any likely devices or compensatory pathways developed by the fetus, except growth restriction, the placenta being the ultimate source of glucose supply. So manifestation of hypoglycemia is earlier and more urgently evident, that further leads to the development of vicious cycle of path ways that can likely worsen the already existent metabolic derangements of hypoxia, hypercapnia, and acidosis.

How ever, for the above four enlisted problems, there are other adaptive devices efficiently developed by the fetus, or else improved by it's normoglycemic status, so that these metabolic derangements are not sensitively felt as hypoglycemia. It was already explained in detail how mere normoglycemia status of the fetus opens the path ways for the lipogenesis, and how this crucial step improves the whole gamut of metabolic derangements caused by placental insufficiency in a cyclically beneficial way, thereby saving molecular oxygen. There are fewmore benefits of lipogenesis that will be mentioned in relevant places in the following discussion.

Hypoxia

Impaired oxygen diffusion across the placenta is also the consequence of placental insufficiency. In the fetus there are many adaptive devices to protect against hypoxia 1. The high affinity of the fetal hemoglobin for oxygen.
2. High fetal cardiac out put, (minute volume) secondary to significant rising of fetal heart rate, in relation to oxygen demand.
3. High RBC (red blood corpuscles) count of the fetus, and also high MCHC (mean corpuscular hemoglobin concentration), resulting in high $O_2$ carrying capacity for unit amount of fetal blood.
4. The fetus operating at the steepest part of the oxygen dissociation curve, with a relatively large amount of oxygen to be released from the hemoglobin.
5. Both the fetal and the maternal oxygen association show changes associated with pH, that give rise to the Bohr effect for oxygen transfer.
6. In fetus glucose can be utilized in Embden-Meyerhof path way of glycolysis which can proceed anaerobically even in the absence of oxygen, to produce pyruvate, lactate, and acetate, which can be utilized by the fetal brain for growth and energy requirements.
7. Even low grade lipogenesis spares the use of molecular oxygen in generating the oxidized coenzymes needed for the major oxidative metabolic path ways, and the triglycerides synthesized during the last months of pregnancy can likely save the fetus a maximum of ⅙ th of the total oxygen requirements, and also the prevention of the use of fats by the fetus for it's energy saves substantial amounts of the oxygen requirements, beta oxidation of lipids being an oxygen consuming path way.

Hypercapnia

Impaired excretion of carbon dioxide ($CO_2$), that is, the exchange of $CO_2$ at the placental site is a reasonable concern in placental insufficiency.

The diffusion coefficient of $CO_2$ is 20 times higher than oxygen, and it's diffusion across the cell membrane including the lipid bi-layer is instantaneous. The progesterone induced maternal hyperventilation leading to fall of maternal $pCO_2$ further compliments the $CO_2$ diffusion across tissue planes. So, the $CO_2$ diffusion across the placenta can be still satisfactory, even when the oxygen diffusion is moderately impaired, and the fetal demise can never be primarily due to hypercapnia.

It is interesting to note that $CO_2$ is required in the initial steps of fatty acid synthesis that involves the carboxylation of acetyl-CoA to melonyl CoA, (made possible by adequate glucose availability). In the synthesis of Palmitate, 7 molecules of $CO_2$ are used, and the same number liberated subsequently from the fatty acid chain. How ever, this cyclic engagement of $CO_2$ from the blood $CO_2$ pool for the fatty acid synthesis, relieves the placenta some of the burden of it's $CO_2$ disposal.

Urea synthesis by the fetus increases as pregnancy advances, and significant amounts of $CO_2$ combine with ammonium in the process of urea synthesis, and it is excreted as the fetal urine into the amniotic fluid. This is also a very important way of significant amounts of $CO_2$ disposal by the fetus in the later months of pregnancy.

Acidosis

Fatty acid synthesis not only generates oxidized coenzymes, but also uses hydrogen ions. 14 hydrogen ions are used in the synthesis of Palmitate from actyl-CoA, and melonyl CoA. During the later month of pregnancy, the amount of lipogenesis that takes place can dispose off enormous amounts of Hydrogen ions from the fetal body. During hypoglycemia, there will not be any lipogenesis. On the other hand, lipolysis and beta oxidation are initiated for energy requirements, further made more prominent by decreased insulin levels due to hypoglycemia. But in the absence of glucose and lack of oxaloacetate, fatty acid oxidation produces ketone bodies which are moderately stronger acids. Once they are formed, even if glucose is made available, the ketone bodies are oxidized in preference to glucose and fatty acids, thus saturating the oxidative machinery.

Accordingly, even when there is enough oxygen, in the absence of glucose, ketone bodies are formed, and the fetus is still going to be acidotic. In the same token, normoglycemia can compensate for hypoxia, but oxygen can not compensate for hypoglycemia, and the related metabolic consequences.

Lactic Acidosis

Insulin increases glucose uptake and glycogen deposition by the placenta, and 80% of placental glycogen is anaerobically metabolized to lactate. It can be freely diffusible across the placenta either into the maternal or fetal circulation, or into the amniotic fluid. By co-transport with hydrogen ions (there is active HMPS in the placenta) lactate is probably transported as lactic acid from the placenta into the fetal circulation. The fetal tissues, especially the fetal brain can utilize lactate, but when it accumulates in excess amounts, it can cause fetal acidosis. Giving the mother IV glucose, during fasting and mid night, avoid the maternal production of ketones (which is not uncommon even in normal pregnancy). Prevention of maternal acidosis can help for more of lactic acid to be disposed of by maternal circulation instead of the fetal circulation, at the placental site.

Production of lactic acidosis can be prevented by initiation of lipogenesis and triglyceride formation during glucose availability, during which time the Glycerol—3 phosphate (the building block of TGD) synthesis from dihydroxyacetone phosphate of gycolysis can be initiated, that involves conversion of $NADH+H^+$ to $NAD^+$, which can be further used in glycolysis, to produce pyruvate rather than lactate. Presumably during glycemic conditions, under the influence of insulin, when lipogenesis is activated, lactate also like pyruvate and acetyl-CoA, is converted into fat.

Amniotic fluid lactic acid level can be a tool likely to assess and control the amount of glucose to be given to the mother, because the raised glycogen content in the placenta will cause enhanced placental lactate production.

The adverse effects of fat utilization by the fetus during hypoglycemia

Adequate amounts of glucose availability precludes the need of utilization of fats for energy requirements in fetuses with uteroplacental insufficiency, and in turn, conserves oxygen. Utilization of fat for energy requirements as in beta oxidation, not only in starvation but also in conditions of normal feeding—probably accounts for about half the total oxygen consumed by the whole body. With out adequate glucose, the fetal body stores of fat are utilized making the hypoxia worse.

As was emphasized earlier, in the absence of glucose, and lack of oxaloacetate, fatty acid oxidation produces ketone bodies which are moderately stronger acids. And once they are formed, even if glucose is made available, the ketone bodies are oxidized in preference to glucose and fatty acids, thus saturating the oxidative machinery.

Fetal hypertriglyceridemia

Econamides and associates (1990) who measured fetal triglyceride (TGD) levels demonstrated fetal plasma hypertriglyceridemia that correlated with the degree of fetal hypoxemia. Barker and colleagues at the united kingdom medical research unit have over 20 years researched the causes of adult mortality and morbidity in relation to possible adverse intra uterine life (Fraser and Cresswell, 1997), and found increased risk of hypertension, and atherosclerosis in the context of IUGR, but no pathogenesis was postulated.

The author inventor attributes the adult hypertension and the atherosclerosis of above studies to the mode of hypertriglyceridemia (it's pathogenesis as also postulated by the author inventor in the subsequent paragraph) produced in the IUGR fetuses that could be persistent for significant part of intrauterine life. Experimental results in animal and human atherosclerosis studies suggest that the fatty streak represents intimal lesions resulting from the focal accumulation of lipoprotein in the vascular intima. Recruitments of leukocytes to the nascent fatty streak, and their adhesion to the vascular intima are further made easier due to sluggish laminar flow because of the polycythemia and hyperviscosity of the blood in IUGR. In this set up, at least some amount of thrombotic reaction in the focal atheromatous area is possible. As per the 'Virchow's triad', the thrombosis of the vessel wall notably depends on 3 factors—the velocity of the blood flow, the viscosity of the blood, and the nature (injury) of the vessel wall, all of which are present in the IUGR fetuses in an adverse manner. Accordingly, in these babies the ground work is already laid, as thrombo-atheromatous plaque in the vessel wall, as an operation of Virchow's triad, in the set up of persistent hypertriglyceridemia in the intra uterine life, that can likely progress and manifest as atherosclerosis and hypertension in adult life. Even a smallest lesion of intra uterine life can be magnified as the baby grows, and in adult life it can assume significant proportion, similar to situations that a mole or a scar on a child's body becoming proportionately bigger in it's adult life.

The initiation and perpetuation of fetal hypertriglyceridemia in IUGR can be postulate as follows—Insulin is a potent positive stimulus for lipogenesis and negative stimulus for lipolysis. It inhibits the activity of the hormone sensitive lipace, reducing the release of not only FFA from the fat stores, but also glycerol. In IUGR there is prolonged and persistent hypoglycemia causing hypoinsulinemia resulting in unopposed action of lipoprotein lipase by other hormones like TSH(Thyroid stimulating hormone), GH (Growth hormone), Glucagon, and ACTH (Adreno-corticotropic hormone), that cause lipolysis. However, because of lack of oxygen needed for beta oxidation of these FFA, the FFA in the blood are not used. As lipogenesis in adipose tissue is prevented by lack of insulin, the esterification of the FFA with glycerol in other tissues results, causing hypertriglyceridemia.

Neonatal hypoglycemia

The level of the circulating glucose just before and soon after birth could be as low as 50 mg % even in apparently normal babies, and it could be worse in placental insufficiency. There is inadequate or absent glycogen stores in the liver, and also impaired fetal ability to release glucose from what ever glycogen stores that are available. Further more, the limited supply of glucose is compromised during delivery, and further cut off after delivery, compounded by explosion of physical activity in different areas of the body, including vigorous crying of the baby following delivery. In anticipation of this problem most obstetricians recommend IV 5% glucose during delivery, and early feeding of the baby after birth.

Vitamins and other essential nutrients

It can be stated that the passage of all the essential nutrients through the placenta are impaired in placental insufficiency. Thiamine and other B-complex factors would not be an exception. Thiamine is essential for carbohydrate metabolism in it's catalytic role of conversion of pyruvate to acetyl CoA, by the pyruvate dehydrogenase complex. If the fetus is deficient in it, substantially increased supply of glucose can be over whelming to the fetus, and can cause accumulation of pyruvate that also can cause lactic acidosis, and all the path ways where glucose and pyruvate are utilized, would come to a halt. Accordingly, planned oral supplementation of 100 mg. of thiamine would increase the levels of thiamine presented at the intervillous space, thus ensuring required amounts reaching fetal circulation. Only small amounts are stored in the body (25-30 mg), and it's daily need increases as the carbohydrate intake increases. This hypothesis of thiamine deficiency of the fetus may not be practically found in all the fetuses with IUGR, but as there is no easy way to know it by certainty, additional supplements at least would not harm. Niacin or nicotinic acid (or Tryptophane, an essential amino acid from which it can be synthesized), from which $NAD^+$ and $NADP^+$ are produced in the body, and Riboflavin, from which FAD (flavin adenine dinucleotide) is produced in the body, are also essential for the carbohydrate metabolism. So also, the folic acid and phosphate supplements are useful. For patients with IUGR, it is therapeutic to advice a diet mostly of carbohydrates, both simple and complex, for immediate and sustained release of hexose sugars, and proteins and fats only as per the pregnancy requirements, but rich in essential amino acids, essential fatty acids, vitamins and minerals—called IUGR diet. The idea is based on the advantage of mostly carbohydrate utilization by the fetus, and likely fat anabolism in the fetal body, and no fat catabolism via beta oxidation, through intrinsic or extrinsic supplies. Snacks of the same formula can also help improving the low blood glucose levels in between meals and midnight.

A case study

It is of practical interest to mention about a successful fetal out come of a severely growth restricted fetus, treated with IV hypertonic glucose. This single case study was done by me, the Author Inventor, in 1984, and is with reference to a primi gravid woman in her early twenties, who was found to have severely growth restricted fetus in the middle of second trimester. She was well nourished, and from good socioeconomic back ground, and there were no obvious etiological factors, or associated medical problems that could account for the IUGR. After observng the growth of the fetus by fundal height for 3-4 more weeks, it was confirmed that the fundal height had not increased, and that the patient undoubtedly had severely growth restricted fetus. As the pregnancy was quite remote from term, and as the bed rest in the left lateral position had not helped, 20% IV hypertonic glucose, 50 cc. twice daily as a bolus was started, and in two to three weeks, there was immediate catch up of fetal growth, and at term, she delivered a healthy baby of normal weight. No adverse effects due to the induced transient maternal hyperglycemia was expected, or was observed through out the pregnancy, and the patient tolerated the treatments very well.

The observed growth restriction was undoubtedly severe, but just with glucose supplementation, the mother delivered a normal healthy fetus at term, and none of the associated problems to be expected due to placental insufficiency like hypoxia, and hypercapnia were found, which could have been evident by at least some amount of fetal distress and lowered apgar score, which also support the fact that in this set up, with mere normoglycemia, the fetus can alleviate multitude of possible metabolic problems by itself.

Intravenous hypertonic glucose treatment to the mother, and induced maternal hyperglycemia When IUGR is first suspected as due to placental insufficiency (having excluded the disease states that would not affect the maternal feto-placental vasculature), the patient has to be hospitalized encouraging bed rest in the left lateral position, and the fetal surveillance started. At a minimum, this includes fetal movement charts, clinical and sonographic assessment of fetal growth, amniotic fluid volume, non stress test, contraction stress test, biophysical profile, daily clinical evaluation of the mother, and frequent fetal heart rate monitoring. Full profile of this exhaustive list of tests is routinely indicated only in the later part of pregnancy. These parameters can be compared to the same readings after IV hypertonic glucose treatment is initiated, as 50-100 cc. bolus twice or thrice daily, of at least 10-20% strength, the detailed clinical protocol of which is not included in this writing.

The trans-amniotic fluid nutritional supplements

Nutritional supplement into the amniotic fluid (AF) is a scientifically attractive proposition, as it avoids the rather uncomfortable situation of interfering with the maternal carbohydrate metabolism. The phenomenon of intrauterine fetal swallowing is taken advantage of in this modality of treatment. 5% isotonic glucose can be safely instilled into the amniotic fluid, with out adversely effecting the osmotic forces.

5% glucose which is isotonic with the extra cellular fluid of the maternal serum should be isotonic with the amniotic fluid, because the normal osmolality of the maternal and the fetal plasma is in the range of 260-275 mosm./kg., and so also is the osmolality of AF from 20-30 weeks of pregnancy. Instillation of 100 cc of 5% glucose twice daily is a supplementation of 10 G. of glucose that would amount to 41 calories to the fetus, and if necessary, it can be administered thrice daily also. Even if AF is replaced every 3 hrs., still substantial amounts can get into the fetal body.

Studies of trans amniotic fetal feeding (TAFF) of pregnant rabbit models were conducted by Mulvihill et al in 1985, using 10% dextrose solution which had been associated with increase in fetal wt. How ever, the studies of Flake et al with solutions of dextrose, amino acids, and lipids alone, or in combination did not reverse the growth restriction, seen in the natural runt rabbit fetus. The reasons for these controversial results can be only postulated. Too much of dextrose, with not enough of required vitamins needed for carbohydrate metabolism (presuming the rabbit's biochemistry as similar to human), could be over whelming to the fetal well being, as already discussed. Too much of lipid supplements, with and with out dextrose, can be a stress to the oxidative machinery of the fetus, as beta oxidation is an oxygen consuming pathway, which would make the existing hypoxia worse, and the co-administration of dextrose not very beneficial.

The technique of trans-amniotic fluid nutritional supplements (TFNS)

The technique of Tran-amniotic Fetal Nutrional Supplements (TFNS) in human subjects is not as easy as it is in animal experiments, because the duration of pregnancy needing supplementation is much longer, and the introduction of infection into the amniotic fluid can be a much feared danger, which is directly proportional to the duration of the needed supplements, and the number of the punctures involved. It is by no means an easy therapeutic endeavor. To make such supplements possible with out the fear of infection, and also to make it practically feasible to both the mother and the obstetrician involved, the recent innovation of implantable ports (originally discovered for central venous access) can be used as a therapeutic device to be inserted over the maternal abdomen, that needs only one time insertion, and is deemed to be functional until the spontaneous or elective delivery of the fetus is done, and the newer version, the Peripherally Inserted Central Catheter (PICC) can be inserted at the patient's bed side also.

Implantable ports are central venous access devices that consists of a subcutaneously implantable reservoir, containing self sealing septum of rubber that can with stand over 2000 needle punctures. In the case of PICC, the reservoir is made up of small titanium port, that is placed in a subcutaneous pocket or tunnel over the maternal abdomen in an easily palpable and easily cleanable location, and accessed using a Huber needle, for withdrawal from withdrawal from or delivery into the amniotic cavity. The port has the advantage of requiring little daily care, and therefore interferes less with the patient's daily activities. The catheter used in this device is a polyurethane catheter placed via an abdominal skin cut down, to be threaded into the amniotic cavity, and can be safely done with ultra sound guidance, to avoid the placenta. However, the whole length of the catheter as used for the central venous access is not needed for uterine access, and only the required length can be cut, depending upon the patient size, to be used for threading. After the access is confirmed, and having at least 5 cm. size of the catheter in the amniotic sac, the catheter is then connected to the titanium port that is placed in the subcutaneous pocket. This design also is an easy maintenance, both by the patient, and the home health care worker.

The sterile patch technique

To make the use of the implantable ports 100% infection free, other novel techniques can be used to make the needle entry site absolutely sterile. During every day use, instead of using the needle on the naked skin of the port site, after cleaning the area thoroughly, a sterile alcohol patch, holding only it's edges while taking out of it's pouch, can be used on the port site, as a sterile skin barrier. The needle can be inserted through the alcohol patch, thus totally avoiding contact with the maternal skin. After the required amount of the nutrients are given, the needle can be taken out, with the alcohol patch still in place. This makes the entry of the needle done totally under aseptic conditions, even if the skin is not thoroughly cleaned, especially if done at the patient's home. How ever, the patient and the home health nurse have to be thoroughly taught about the danger of infection if not done as instructed, and wearing sterile gloves, still has to be practiced during the use of the port even with the alcohol patch.

The trans-Amniotic fetal nutritional supplements in clinical practice

The amount of 5% dextrose that needs to be instilled into the amniotic cavity of a patient should be individualized. It could be detrimental to the fetus, if too much of 5% glucose is supplemented in situations of severe placental insufficiency when hypoxia can be severe, that could lead to anaerobiasis and lactic acidosis that the fetus can not handle. It can be a therapeutic option that 5 L of $O_2$ by nasal canula, can be administered to the mother during and for 2-4 hours after the glucose supplementation, but not continuously. Research studies on $O_2$ administration were done that yielded controversial results. The oxygen, during the increased supply of glucose, would help aerobic glycolysis of the administered carbohydrate. It is a good idea to start with small amounts of glucose supplements and progressively increase. Until the glucose required by any mother with an IUGR fetus can be determined, monitoring the AF lactic acid levels is a good idea, as very high levels could be a reflection of too much glucose that the fetus can not handle. The danger of excessive glucose supplements to a hypoxic fetus is more in this type of supplements, because at least in IV glucose supplementation, the amount that gets to the fetus is controlled by the placenta, that would be directly proportional to the severity of hypoxia secondary to the placental insufficiency.

How adequate glucose availabitly compensates for relative lack of oxygen and other metabolic provisions is summarized as follows 1) Adequate glucose availability induces $NAD^+$ regenerating lipogenesis' through the function of dehydrogenase enzyme complexes, thereby making $NAD^+$ available for glycolysis, to produce pyruvate rather than lactate, thus glucose compensating for relative lack of oxygen.
2) Adequate glucose availability in the fetus causes coupling of lipogenesis and glycolysis-citric acid cycle, wherein the oxidized co-enzymes $NAD^+$ and $NADP^+$ regenerated through lipogenesis cause
   (a) glycolysis to continue, by regenerated oxidized $NAD^+$ converting glyceraldehyde 3-phosphate to 1, 3 biphospho glycerate,
   (b) glucose helping it's own metabolism to completion, by proceeding into ATP generating citric acid cycle', despite relative hypoxia,
   (c) HMPS to continue, by oxidized $NADP^+$, regenerated by means of fatty acid synthesis.
3) By adequate availability, glucose at different steps of it's own metabolism diverts $NADH+H^-$ to lipogenesis, from an otherwise obligatory aerobic oxidative phosphorylation, consistent with the fetus requiring more growth and less ATP.
4) Adequate glucose availability induces preferential carbohydrate catabolism in the fetus, thereby obviating beta oxidation of lipids, a high oxygen consuming path way.
5) Adequate glucose availability furthermore relieves fetal hypoxia (by means as mentioned above), fetal hypercapnia, and fetal acidosis including the ketoacidosis and lactic acidosis.

The rationale for glucose supplemental treatment instead of planned early delivery of untreated IUGR fetus
1. The intravenous hypertonic glucose (dextrose) treatment to the mother is easier, physically and emotionally less traumatic, and less invasive, compared to the treatment modalities involved in caring for the premature IUGR baby in the NICU (neonatal intensive care unit).
2. The incidence of cesarean section is likey to be more for the elective preterm delivery of the IUGR fetus, with it's associated complications to the mother, especially when there are likely accompanying medical problems also.
3. Uncertainties of clinical out come of the untreated IUGR fetus, and the anxiety that is unavoidable for both the parents and the obstetrician can be over come by likely delivering a grown and physiologically mature baby with treatment.
4. Cognition—though the literature mentions that severe disabilities are low with deliveries as early as 34-36 weeks, even mild disabilities like ADHA (attention deficit and hyperactivity) is a significant problem, especially if it can be avoidable. There is no way to know what the child's IQ (intelligence quotient) 'would have been' if the intra uterine stay were to be prolonged and the IUGR treated. For the cognitive evaluation of the baby during subsequent years after birth, the right comparable parameter of the child's genetic IQ is never known, to be compared to it's phenotypical IQ, to know what the child is actually missing. Evidently, the most important parameters of comparison is missing, and one can only say that the child is not mentally retarded, but can not say how much IQ drop had likely resulted. The comparison with the general population is not statistically accurate, because the comparison here involves the individual child's genetic (inherent) and phenotypical (acquired) IQ. Even siblings of the same parents can be very different in their cognitive endowment that a right or relevant comparison can not be expected to be made with general population.
5. The purposed treatment to the mother afflicted with IUGR fetus is cost effective.
6. Termination of the untreated IUGR pregnancy early, and the subsequent management of the premature growth restricted baby can be done only in well equipped centers with NICU, and the hospitalization can be long, but the proposed treatment of the mother with afflicted IUGR fetus can be done even in small settings. In motivated intelligent patients the treatment can be done at home also, with the help of the home health nurse.
7. Only few complications attributable to preterm deliveries were found to be indistinguishable from the term delivery, between 32-34 weeks. The incidence of the respiratory distress syndrome was found to be as high as 6% even at 35-38 weeks of delivery.
8. Neonatal hypoglycemia, polycythemia, and hyperviscosity of the blood (the later two secondary to chronic hypoxia) can be avoided with intravenous hypertonic glucose supplements to the mother, and prolonging intrauterine stay of the fetus. Early diagnosis of IUGR, and treating with glucose will also prevent fetal hypertriglyceridemia, and, as mentioned in the recent studies, the further development of hypertension and atherosclerosis as well, in the adult life.
9. It should be the aim of the obstetrician to not only deliver a seemingly normal child, but also a child with the full potential it is genetically endowed with.

The elaborate biochemical discussion was necessary, because it has many clinical implications that need to be understood by the practicing clinician, without which confident and intelligent management of the IUGR fetus and it's mother can not be optimal.

DEDICATION

This work is dedicated to the memory of late Dr. Arthur Guyton C., MD., a great physiologist and author, and more importantly, through his widely read writing of the 'Text Book of Medical Physiology', remained as a teacher and mentor to great many all around the world.

REFERENCES FROM NON-PATENT RELATED LITERATURE

1. Guyton Arthur C—Transport though cell membrane—Text Book of Medical Physiology, $6^{th}$ edition, 1980.
2. Raiha—Tissue Metabolism In Human Fetus, Cold Spr. Harb. Symp. Quant. Bio., 1954, 19, 143.
3. Ville C. A—The Intermediary Metabolism of Human Fetal Tissue—Cold Spr. Harb. Symp. Quant. Biol., 1954, 19, 143.
4. Jean Ginsberg—Carbohydrate Metabolism—The Text Book of 'Scientific Foundations of Obstetrics and Gynecology'—First Edition, 1970.
5. Myant N. B.—Lipid Metabolism—The Text Book of 'Scientific Foundations of Obstetrics and Gynecology'—First Edition, 1970.
6. Roux—Lipid Metabolism in Fetal and Neonatal Rabbits—Metabolism, 1966, 15, 856.
7. Fraser and Crosswell J.—What should Obstetricians be doing about the Barker's Hypothesis·.·—Brit. J. Obstet. Gynecol., 104:645; 1997.
8. Econamides D. L., Crook D., Nicolaides KH.—Hypertriglyceridemia and Hypoxemia in Small for Gestational age Fetuses—Am J. Obstet. Gynecol, 162:387, 1990.

9. Mulvihill S. J., Albert A., Synn A., Fonkalsrud—In utero Supplemental Fetal Feeding in the Animal Model: Effect on Fetal Growth and Development, Surgery 1985; 98:500-505.
10. Flake A. W, Villa R. L., Adzick N. S., Harrison M. R.—Transamniotic Fetal Feeding III. A Model of Intrauterine Growth Retardation using the Relationship of 'Natural Runting' to Uterine Position—Journal of pediatric surgery 1987; 22, issue 9:816-819.
11. Rapheal N. Pollack, Haim Yafee, Michael Y. Divon—Therapy for Intrauterine Growth Restriction:Current Options and Future Directions—Clinical Obstetrics and Gynecology, volume 40, No. 4, December 1997, 824-842.
12. David W. Martin, Peter A. Mayes, Victor W. Rodwell, Gerold M. Grodsky—Harper's Review of Biochemistry, 19$^{th}$ edition.
13. Robert K. Murray, Daryl K. Granner, Peter A. Mayes, Victor W. Rodwell—Harper's Illustrated Biochemistry, 26$^{th}$ edition.

The claims are for:

1. A method of treatment for human fetal intra uterine growth restriction (IUGR) due to vascular insufficiency of placental origin, involving a modality of administering a 50-100 cc. bolus of at least 10-20% intravenous hypertonic glucose twice or three times in a day, to a pregnant patient carrying said fetus, sufficient to produce transient and episodic maternal hyperglycemia resulting in increased amount of glucose in the placental and fetal circulation.

2. The method of claim 1, wherein the therapeutically induced maternal hyperglycemia causes accelerated facilitated diffusion of glucose across the placenta, relieving fetal hypoglycemia resulted from compromised blood flow of varying causes across the placental interface.

3. The method of claim 2, wherein the therapeutically induced transient maternal hyperglycemia further causes maximal function in a sub maximally operating carrier protein at the placental interface, and results in the saturation of facilitated diffusion of glucose across the placenta subject to the said carrier protein, through a stereospecific, non-concentrating process.

4. The method of claim 1, wherein the therapeutically induced maternal hyperglycemia causes normoglycemic status in the said fetus, the said normoglycemic status of the fetus subject to initiation and maintenance of fetal lipogenesis, the said lipogenesis effectuating a means of generating the oxidized forms of NAD$^+$ and NADP$^+$ for the fetal carbohydrate metabolic pathways, through dehydrogenase enzyme complexes involving anaerobic oxidative process, a mechanism of coupling of lipogenesis and glycolysis-citric acid cycle with in the fetus, said mechanism saving molecular oxygen subject to generating ATP, involving obligatory aerobic process.

5. The method of claim 1 of administering intravenous hypertonic glucose to a pregnant patient with fetal IUGR for inducing transient maternal hyperglycemia, further comprising supplementing 100 mg. of thiamine to said pregnant patient with said fetal IUGR, wherein the induced normoglycemia in the fetus generates acetyl-CoA to interact with oxaloacetate in amounts sufficient to continue into and sustain the citric acid cycle, and further for the malate shuttle to become operative with in the fetus, regenerating needed oxidized NAD$^+$ for the aerobic glycolysis to continue in the cytosol, despite relative hypoxia.

6. The method of claim 1, wherein the induced fetal normoglycemia is operative in obviating beta oxidation of the fetal free fatty acids averting ketoacidosis within the fetus, and further the insulin resulting from normoglycemic status of the fetus exerting an antilipolytic effect, averting beta oxidation of fetal fat catabolism.

7. The method of claim 4, wherein the method further results in improvement of fetal hypercapnia, wherein carbon dioxide is transiently engaged in the fetal fatty acid synthesis cycle, thereby relieving the burden of some carbon dioxide disposal at the placenta interface.

8. The method of claim 1, wherein the method alleviates the following conditions within the fetus
   a) ketoacidosis, by means of obviating fat catabolism operative in generating moderately stronger ketoacids, and obviating fat catabolism with in the fetus, further averting saturating the oxidative machinery,
   b) fetal acidosis, by means of inducing fetal lipogenesis utilizing hydrogen ions, in a greater extent from the hexose monophosphate shunt, 14 molecules of hydrogen ions participating in synthesizing a single molecule of palmitate, said initiating of hexose mono phosphate shunt in turn induced by fetal normoglycemic status,
   c) lactic acidosis, by means of coupling reactions converting glyceraldehyde 3-phosphate to 1,3 biphosphoglycerate, and dihydroxy acetone phosphate to glycerol 3-phosphate involving fetal lipogenesis, causing NADH+H$^+$ getting oxidized to NAD$^+$, the said NAD$^+$ further inhibiting the fetal glycolytic reduction of pyruvate to lactate.

9. The method of claim 4, wherein the method improves fetal hypoxia by
   a) causing coupling of lipogenesis-glycolysis citric acid cycle with in the fetus, wherein the oxidized co-enzyme NAD$^+$ resulting from forming glycerol 3 phosphate as the binding block in fetal lipogenesis causes glycolysis to continue, converting glyceraldehyde 3 phosphate to 1,3-biphosphoglycerate, thereby producing pyruvate, despite fetal hypoxia,
   b) the glucose inducing fetal lipogenesis, and generating the oxidized form of NAD$^+$, compensating for the lack of oxygen,
   c) obviating fat utilization within the fetus, and utilizing carbohydrate, in a less oxygen consuming pathway,
   d) diverting NADH+H$^+$ from fetal aerobic oxidative phosphorylation to fetal anaerobic oxidative lipogenesis.

10. The method of claim 1, wherein the therapeutic maternal hyperglycemia inducing fetal normoglycemia generates adequate oxaloacetate and acetyl-CoA within the fetus, and further diverts dihydroxy acetone phosphate and NADH+H$^+$ for fetal lipogenesis, consistent with increased fetal growth, and it's reduced ATP requirement.

11. The method of claim 1, wherein the timed maternal intravenous hypertonic glucose administration restores maternal normoglycemia between meals and midnight, alleviates maternal ketoacidosis, facilitates preferential disposal of lactic acid from placenta into maternal circulation, thereby averting fetal lactic acidosis.

12. The method of claim 1, wherein the therapeutic maternal hyperglycemia causing fetal normoglycemia initiates fetal lipogenesis, producing glycerol 3-PO$_4$ along with continuous generation of oxidized coenzyme NAD$^+$, said NAD$^+$ further participating in fetal glycolysis, thereby inhibiting conversion of pyruvate to lactate.

13. The method of claim 1, wherein the therapeutically induced maternal hyperglycemia causing fetal normoglycemia averts fetal hypertriglyceridemia by the said fetal normoglycemic status producing adequate insulin, thereby antagonizing lypolytic action of the enzyme lipoprotein lipase.

14. The said method of claim 1, further comprising administering to the mother a diet composed primarily of: simple and complex carbohydrates causing both rapid and sustained release of hexose sugars; fats and proteins as per pregnancy requirements; high amounts of essential amino acids and essential fatty acids; and a rich contribution of B-complex factors and minerals, said diet resulting in the fetal carbohydrate catabolism and fat anabolism, thereby averting beta oxidation, a high oxygen consuming path way.

15. The method of claim 1, comprising the steps of:
a) inducing transient therapeutic hyperglycemia in a pregnant patient with the said IUGR fetus, by administering to the mother 50-100 cc. bolus of at least 10-20% intravenous hypertonic glucose twice or thrice in a day, wherein the induced transient maternal hyperglycemia increases glucose concentration at the placental interface, thereby saturating the sub-optimally functioning carrier protein for the facilitated diffusion of D-glucose, and
b) further supplementing the maternal diet with a diet comprising primarily simple and complex carbohydrates, with a rich contribution of essential fatty acids and essential amino acids, the non essential components being subject to mere pregnancy requirements, and the diet further comprising also rich supplements of vitamin B-complex factors and minerals.

16. The method of claim 1, wherein the administered bolus hypertonic glucose to the mother is at a concentration of 10-20%.

* * * * *